United States Patent [19]

Winkley et al.

[11] Patent Number: 4,755,505
[45] Date of Patent: Jul. 5, 1988

[54] 1-[2-(DIALKYLAMINO)ALKYL]-4,5-DIHYDRO-4-(ARYL)-1-BENZAZOCINE-2,6(1H,3H)-DIONES AS ANTI-ARRHYTHMIC AGENTS

[75] Inventors: Michael W. Winkley, Malvern; James L. Diebold, Norristown, both of Pa.

[73] Assignee: American Home Products Corporation, New York, N.Y.

[21] Appl. No.: 86,754

[22] Filed: Aug. 18, 1987

[51] Int. Cl.[4] .................. A61K 31/395; C07D 225/06
[52] U.S. Cl. .................................... 514/183; 540/461; 540/463
[58] Field of Search ................. 514/183; 540/461, 463

[56] References Cited

U.S. PATENT DOCUMENTS 4,537,885  8/1987  Watthey .............................. 540/461
4,684,645  8/1987  Chang et al. ........................ 540/461

FOREIGN PATENT DOCUMENTS 4945874  5/1970  Japan ................................. 540/463
5683477  12/1979  Japan ................................. 514/183

OTHER PUBLICATIONS

Witkop et al., "J. Am. Chem. Soc.", vol. 73, pp. 2641-2647 (1951).

Primary Examiner—Robert T. Bond
Attorney, Agent, or Firm—Arthur G. Seifert

[57] ABSTRACT

Disclosed herein are new 4-aryl-benzazocine-2,6-diones of Formula I

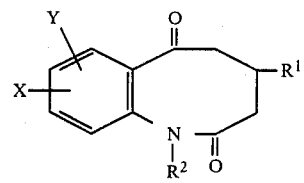

in which $R^1$ is phenyl, naphthyl or phenyl or naphthyl substituted by one to three moieties selected from fluoro, chloro, bromo, and alkyl or alkoxy of 1 to 4 carbon atoms;

$R^2$ is $-R^3-NR^4R^5$, wherein $R^3$, $R^4$ and $R^5$ are, independently, straight or branched chain alkyl groups of 1 to 4 carbon atoms or $R^4$ and $R^5$ are concatenated to form nitrogen ring having 3 to 8 carbon atoms; and X and Y are, independently, hydrogen, alkyl or alkoxy of 1 to 4 carbon atoms, dialkylamino or dialkylcarboxamido wherein each alkyl group has 1 to 4 carbon atoms, cyano, alkylacyl of 1 to 4 carbon atoms, fluoro, chloro, nitro, dialkylsulfonamido wherein each alkyl group has 1 to 4 carbon atoms, or alkylsulfonyl of 1 to 4 carbon atoms, or a pharmaceutically acceptable salt thereof.

The compounds of Formula I are useful as anti-arrhythmic agents.

18 Claims, No Drawings

1-[2-(DIALKYLAMINO)ALKYL]-4,5-DIHYDRO-4-(ARYL)-1-BENZAZOCINE-2,6(1H,3H)-DIONES AS ANTI-ARRHYTHMIC AGENTS

The invention described herein concerns new chemical compositions and, in particular compounds having the formula I.

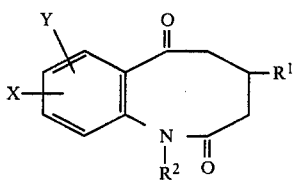

In formula I, $R^1$ may be aryl (e.g., phenyl, naphthyl) or substituted aryl (e.g., chlorophenyl, trimethyloxyphenyl, methylnaphthyl). $R^2$ is the group:

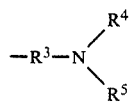

wherein $R^3$, $R^4$ and $R^5$ are lower straight-chain or lower branched-chain alkyl. By "lower alkyl" is meant an alkyl group having 1–8 carbon atoms. $R^4$ and $R^5$ can also be concatenated to form a heterocyclic nitrogen ring containing up to 8 carbon atoms. X and Y may be hydrogen, lower alkyl, lower alkoxy, lower alkylamino, carboxamido, cyano, lower acyl, halogen, nitro, sulfonamido, or lower alkylsulfonyl. The compounds of Formula I of the invention exhibited antiarrhythmic and calcium antagonism in standard pharmacological procedures. The invention also includes a method of treating mammals, including man, afflicted with heart arrhythmia by administering an amount of a compound of Formula I effective to alleviate the arrhythmia.

BACKGROUND OF THE INVENTION

Benzazocine-2,6-diones unsubstituted on the dione ring were reported by Jones and Tringham, Journal of the Chemical Society Perkins, I, 1280–1283 (1975), as intermediates for possible anti-inflammatory agents. The desired end products therein had a carboxylic acid group in place of the oxo group in the six position and an aralkyl group on the nitrogen—and were found to exhibit no significant anti-inflammatory activity.

3-Amino-benzazocine-2,6-diones having angiotensin converting enzyme inhibition and hypotensive properties are disclosed in European Patent Publication EP-119-161-A to Ciba-Geigy (Derwent Abstract 84-232700/38). These compounds are further substituted on the nitrogen atom by a methylene carboxy group.

The new compounds of the invention differ from the above in having a 4-aryl or heteroaryl substituent and 1-alkyleneamino substituent. Further, the new compounds of the invention exhibits pharmacological properties as anti-arrhythmic agents.

DETAILED DESCRIPTION OF THE INVENTION

The first aspect of this invention provides new 4-aryl-benzazocine-2,6-diones of Formula I

in which
  $R^1$ is phenyl, naphthyl or phenyl or naphthyl substituted by one to three moieties selected from fluoro, chloro, bromo, and alkyl or alkoxy of 1 to 4 carbon atoms;
  $R^2$ is $—R^3—NR^4R^5$, wherein $R^3$, $R^4$ and $R^5$ are, independently, straight or branched chain alkyl groups of 1 to 4 carbon atoms or $R^4$ and $R^5$ are concatenated to form nitrogen ring having 3 to 8 carbon atoms; and
  X and Y are, independently, hydrogen, alkyl or alkoxy of 1 to 4 carbon atoms, dialkylamino or dialkylcarboxamido wherein each alkyl group has 1 to 4 carbon atoms, cyano, alkylacyl of 1 to 4 carbon atoms, fluoro, chloro, nitro, dialkylsulfonamido wherein each alkyl group has 1 to 4 carbon atoms, or alkylsulfonyl of 1 to 4 carbon atoms,
or pharmaceutically acceptable salts thereof.

A second aspect of this invention provides a method of treating heart arrhythmia in mammals, including man, having a heart arrhythmia, comprising administering to such mammal in need thereof an amount of a compound of Formula I effective to alleviate said arrhythmia.

Preferred compounds of both aspects of the invention are those in which: $R^1$ is phenyl or naphthyl unsubstituted or substituted as described for Formula I; $R^3$ is methylene or ethylene; $R^4$ and $R^5$ are methyl or ethyl or $—NR^4R^5$ is pyrrolidine, piperidine, or hexamethylimine ring; and X and Y are hydrogen, lower alkyl or lower alkoxy of 1 to 3 carbon atoms, fluoro, chloro, or X is one of the foregoing and Y is hydrogen. Particularly preferred compounds of both aspects of the invention are those in which $R^1$ is phenyl, naphthyl, methoxyphenyl, chlorophenyl, trimethyloxyphenyl, or methylnaphthyl; $R^3$ is ethylene; $R^4$ and $R^5$ are methyl; and X and Y are hydrogen.

The following reaction scheme depicts suitable processes for preparing the compounds of Formula I

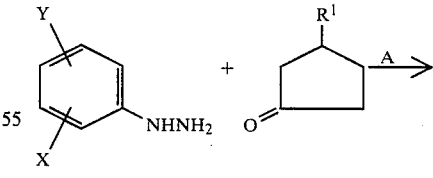

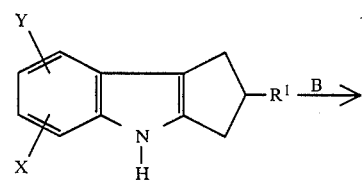

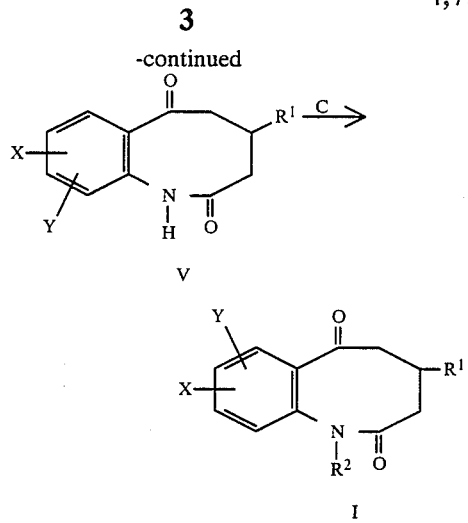

In process step A, an appropriately substituted phenylhydrazine (II) is reacted with an appropriately substituted cyclopentanone (III) under acidic conditions. Suitable reaction conditions are described by R. B. Perni and G. Gribble in Orgaic Preparations and Processes International, 14, 343–346 (1982). A mixture of 1 and 2 substituted ($R^1$) 1,2,3,4-tetrahydro-cyclopentyl[b]indoles is obtained, and the desired 2 isomer (IV) is isolated for step B. (Or, separation of the desired isomer may take place at the end of steps B or C).

In step B, oxidation of the 2-substituted-1,2,3,4-tetrahydro-cyclopentyl[b]indole thus obtained may be accomplished using m-chloroperbenzoic acid as an oxidant in accordance with the procedure of V. Dave and E. W. Warnoff, Canadian Journal of Chemistry, 50, 3392–3396 (1972). Other suitable oxidation conditions compatible with values of $R^1$, X and Y other than those exemplified are known to the art-skilled organic chemist. In step C, the $R^2$ moiety may be conveniently introduced. For example, the appropriate dialkylaminoalkyl halide (chloride or bromide) or pyrrole or pyridyl-alkyl halide may be reacted with V in an inert solvent, such as toluene, in the presence of a suitable amount of sodium hydride to yield the desired product of Formula I.

The pharmacologically acceptable salts of the compounds of this invention are prepared directly by neturalization of the free base. These salts may be formed with organic or inorganic acids such as hydrochloric, hydrobromic, phosphoric, sulfuric, sulfurous, nitric, methylsulfonic, acetic, maleic, succinic, fumaric, tartaric, citric, salicylic, lactic, naphthalene-sulfonic acid, and the like.

The compounds of this invention demonstrate antiarrhythmic activity when tested in the standard experimental animal in accordance with the following procedure [Bergey, J. L., et al., European Journal of Pharmacology, 81, 205–216 (1982)]:

Rats weighing between 400–500 gms were anesthesized with 35–40 mg/kg sodium pentobarbital intraperitoneally. Rats were close-clipped on the neck and left thorax prior to cannulation of the jugular vein and carotid artery for measurement of arterial blood pressure and injection of drug. A tracheotomy was performed and respiration provided by a Harvard Model 681 respirator at a rate of approximately 55 cycles/min and a volume of 4 cc per cycle. The rat was then placed upon its right side and the heart was exposed by making an incision and separating the ribs. 4-0 Silk on taper RB-1 needle was passed under the left anterior descending coronary artery (LAD) at a location just under the tip of the left atrial apendage. The suture was left to be tied upon occlusion.

The rat was allowed to stabilize for 5 to 15 minutes before the administration of drug as a bolus via the cannulated jugular vein. The total drug dose volume is kept constant between 0.20–0.25 ml. Fifteen minutes after dosing, the LAD was occluded by tying the suture. This procedure provokes severe ventricular arrhythmias, terminating in ventricular fibrillation and death in at least about 65 percent of animals given vehicle only. The development and progression of ventricular arrhythmia is monitored for a period of 20 minutes. Lead II ECG and cardiotachometer output were recorded on a Beckman R612 recorder.

Mean arterial pressure (MAP) is monitored throughout the experiment, and the following values recorded: (1) MAP prior to drug, (2) maximal change in MAP following drug and before LAD occlusion, and (3) MAP just prior to LAD occlusion. Changes in cardiac electrical activity are determined from the Lead II electrocardiogram. The dysrhythmias are scored as follows: (1) normal sinurhythm, (2) isolated premature ventricular complexes, (3) non-sustained ventricular tachycardia (repetitive beats of ventricular origin lasting 15 sec.), (4) sustained ventricular tachycardia (repetitive ventricular activity lasting 15 sec.), (5) self-terminating or reversible ventricular fibrillation (VFrev), and (6) irreversible VF (VF irrev. death). The incidence of death in the drug-treated group is then compared to that in the untreated control group (generally 65%). Five animals are included in each drug group.

Arrhythmias scores are calculated for each group of animals for purposes of obtaining more quantitative rankings for anti-arrhythmic efficacy. The equation, $$\sum_{n=1}^{i} A \times AS,$$

is used, where A=fraction of animals with a certain kind of arrhythmia (e.g., ventricular fibrillation, sustained ventricular tachycardia) and AS is the arbitrary score assigned to that arrhythmia:

|     | A                                    | AS  |
|-----|--------------------------------------|-----|
| (a) | no arrhythmia                        | −5  |
| (b) | isolated premature beats (PVC's)     | +5  |
| (c) | non-sustained ventricular tachycardia| +10 |
| (d) | sustained ventricular tachycardia    | +20 |
| (e) | reversible ventricular fibrillation  | +40 |
| (f) | death                                | +50 |

Thus, for the purpose of these coronary ligation (C.L.) experiments, a score from −5 (no arrhythmia) to 50 (death) is assigned to the response of each rat in a test group, based upon the number, type and severity of each response. The sum of the percent of animals at each response level times the point score assigned that response level equals the score value of the compound being tested. The lower the score, the more active the compound in preventing ventricular dysrhythmia.

In this procedure the compound of Example 8 had a score of 15 when administered at 10 mg/kg of body weight. This activity score is considered moderate. The corresponding 1-[2-(dimethylamino)ethyl]-4,5-dihydro- 5-(4-methoxyphenyl)-1-benzazocine-2,6-(1H,3H)-dione was inactive when similarly tested.

This pharmacological property of the compounds of the invention indicates that they would be useful in the treatment of cardiac arrhythmias and conditions characterized by coronary artery occlusion and the resulting myocardial ischemia. For that purpose, the compounds may be administered orally or parenterally in suitable dosage forms compatible with the route of administration, whether oral, intraperitoneal, intramuscular, intravenous, intranasal, buccal, etc.

For treatment of such conditions the compounds of the invention on their pharmacologically acceptable salts may be administered in doses of 1 to 100 milligrams per kilogram of the host body weight in single or plural doses as needed to relieve the arrhythmic dysfunction.

The specific dosage regimen for a given patient will depend upon age, patholigical state, severity of dysfunction, size of the patient, etc. Oral administration is performed with either a liquid or solid dosage unit in any conventional form such as tablets, capsules, solutions, etc. which comprise a unit dose (e.g. from about 25 milligrams to about 4 grams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizer, preservatives and emulsifiers.

Preparation of the compounds of the invention and their salts is further illustrated by the following examples.

EXAMPLE 1

1,2,3,4-Tetrahydro-2-(4-Methoxyphenyl)Cyclopent[b]Indole

A mixture of 3-(4-methoxyphenyl)-1-cyclopentanone (15.22 g) and phenyl hydrazine hydrochloride (11.57 g) in glacial acetic acid (112 ml) under nitrogen was stirred magnetically and slowly heated to 90° with a heating mantle. A white precipitate, which formed at approximately 60°, dissolved to give a red solution as the temperature rose exothermically to 110°. As soon as the solid had dissolved, the heating mantle was removed and the temperature allowed to return to 90° for 1 hr. The cooled solution was poured into 400 ml of water. After refrigeration, the supernatant liquid was filtered. The filter pad and residual material were dissolved in chloroform and the solution was washed with saturated sodium bicarbonate solution. The dried (MgSO$_4$) solution was evaporated to a syrup which was subjected to an oil pump vacuum; wt. 19.4 g (92%). This material was chromatographed on a column (60×7.6 cm) of silica gel prepacked in chloroform. Elution with chloroform afforded a mixture of the titled product and 1,2,3,4-tetrahydro-1-(4-methoxyphenyl)-cyclopent[b]indole in a ratio of 3:2 as determined by a reverse phase HPLC system (see Example 2). After solvent removal the residual syrup was coevaporated with acetonitrile to give 11.90 g (56.5%) of a red syrup which began to crystallize on standing. Crystallization from acetonitrile-water (seeding) gave crude product; wt. 5.25 g (24.9%), mp=107°–109°. Recrystallization from acetonitrile-water gave the titled product as pale yellow crystals, wt. 4.39 g, mp=109°–111°.

Analysis: C$_{18}$H$_{17}$NO: Calculated: C, 82.10; H, 6.51; N, 5.32. Found: C, 82.24; H, 6.58; N, 5.14.

The mother liquor from the first crystallization of the titled product was evaporated to a syrup and subjected to an oil pump vacuum; wt. 6.7 g. The ratio of titled product to 1,2,3,4-tetrahydro-1-(4-methoxyphenyl)cyclopent[b]indole in this material was 36:64 as determined by HPLC.

EXAMPLE 2

1,2,3,4-Tetrahydro-1-(4-Methoxyphenyl)Cyclopent[b]Indole

The material from the mother liquor obtained in Example 1 was subjected to preparative reverse phase chromatography on two C$_{18}$ Prep Pak 500 (Waters) columns in tandem. Elution was with acetonitrile-water (47:53). Fractions (usually 1 l.) were monitored by anaytical HPLC on a Waters $-Bondpak C18 column using acetonitrile-water (1:1) as solvent. The first component to issue from the column was the titled compound. Appropriate fractions were combined and evaporated until an emulsion was obtained. After addition of salt and brine to the mixture it was extracted several times with dichloromethane. The organic extract was washed with brine and dried (MgSO$_4$). The resulting syrup was coevaporated with acetonitrile and crystallized from acetonitrile-water; wt. 2.75 g (13.1%), mp=107°–109°. Recrystallization from acetonitrile-water affored pure titled product as pale yellow crystals; wt. 2.32 g, mp=108°–109°.

Analysis for: C$_{18}$H$_{17}$NO: Calculated: C, 82.10; H, 6.51; N, 5.32. Found: C, 82.49; H, 6.47; N, 5.37.

Later fractions from the preparative HPLC were similarly processed to give additional 1,2,3,4-tetrahydro-2-(4-methoxyphenyl)cyclopent[b]-indole; wt. 1.24 g (5.9%), mp=110°–112°.

Analysis for: C$_{18}$H$_{17}$NO: Calculated: C, 82.10; H, 6.51; N, 5.32. Found: C, 81.91; H, 6.52; N, 5.29

EXAMPLE 3

1,2,3,4-Tetrahydro-2-(4-Methoxyphenyl)Cyclopent[b]Indole

A mixture of 3-(4-methoxyphenyl)-1-cyclopentanone (15.22 g) and phenyl hydrazine hydrochloride (11.57 g) in glacial acetic acid (112 ml) under nitrogen was stirred magnetically and slowly heated to 90° with a heating mantle. A white precipitate, which formed at approximately 60°, dissolved to give a red solution as the temperature rose exothermically to 110°. As soon as the solid had dissolved, the heating mantle was removed and the temperature allowed to return to 90°. The temperature was then maintained at 90° for 1 hr. The cooled solution was poured into 400 ml of water. After refrigeration, the supernatant was filtered. The filter pad and residual material were dissolved in dichloromethane and the solution was washed with saturated sodium bicarbonate solution. The dried (MgSO$_4$) solution was evaporated to a syrup which was subjected to oil pump vacuum; wt. 20.1 g (95%).

This crude material in dichloromethane was applied to a column (79×8.4 cm) of silica gel prepacked in dichloromethane. Elution with dichloromethane afforded a mixture of the titled product and 1,2,3,4-tetrahydro-1-(4-methoxyphenyl)cyclopent[b]indole. After solvent removal, the residual yellow syrup (12.5 g) was coevaporated with acetonitrile to obtain a syrup which was crystallized from acetonitrile-water (seeding); wt.

5.99 g (28.4%), mp=106°-109°. Two crystallizations gave pure titled compound having mp=111°-112°.

Analysis for: $C_{18}H_{17}NO$: Calculated: C, 82.10; H, 6.51; N, 5.31. Found: C, 81.93; H, 6.68; N, 5.13.

The mother liquor from the first crystallization of the titled product was evaporated to a syrup which was coevaporated with acetonitrile. The yellow resulting syrup was dried under oil pump vacuum; wt. 6.3 g. This material was used in Example 4.

EXAMPLE 4

4,5-Dihydro-5-(4-Methoxyphenyl)-1-Benzazocine-2,6(1H,3H)-Dione

To a stirred solution of the syrupy material (6.3 g) isolated from the mother liquors in Example 3 in dichloromethane (150 ml) at 10° was added slowly m-chloroperbenzoic acid (14.6 g) in dichloromethane (350 ml) and the mixture was stirred at room temperature overnight. The solution was washed consecutively with 10% sodium sulfite solution, saturated sodium bicarbonate solution and brine and dried ($MgSO_4$). Evaporation gave a residue which was subjected to an oil pump vacuum; wt. 6.6 g. Slurrying with acetone gave a tan solid, wt. 2.38 g (10%), mp=230°-233°. Recrystallization from acetonitrile gave 1.60 g [6.8% from 3-(4-methoxyphenyl)-1-cyclopentanone] of pure titled compound, mp=245°-246°.

Analysis for: $C_{18}H_{17}NO_3$: Calculated: C, 73.20; H, 5.80; N, 4.74. Found: C, 73.24; H, 5.75; N, 4.76.

EXAMPLE 5

1,2,3,4-Tetrahydro-2-(4-Methoxyphenyl)Cyclopent[b]Indole

A mixture of 3-(4-methoxyphenyl)-1-cyclopentanone (15.21 g) and phenylhydrazine hydrochloride (11.56 g) in glacial acetic acid (110 ml) under nitrogen was stirred magnetically and slowly heated to 90° with a heating mantle. A white precipitate, which formed at approximately 60°, dissolved to give a red solution as the temperature rose exothermically to 110°. As soon as the solid had dissolved, the heating mantle was removed and the temperature allowed to return to 90°. The temperature was then maintained at 90° for 1 hour. The cooled solution was poured into water (400 ml). After refrigeration under nitrogen overnight, the supernatant liquid was filtered. The filter pad and residual material were dissolved in dichloromethane and the solution was washed with saturated sodium bicarbonate solution. The dried ($MgSO_4$) solution was evaporated to a syrup which was subjected to an oil pump vacuum; wt. 18.7 g. This material in dichloromethane was chromatographed on a column of silica gel prepacked in dichloromethane. Elution with dichloromethane afforded a mixture of the titled product and 1,2,3,4-tetrahydro-1-(4-methoxyphenyl)cyclopent[b]indole. After solvent removal, the residual yellow syrup was crystallized from ethanol-hexane to give the titled product as pale yellow crystals; wt. 5.14 g (24.4%), mp=108°-110°.

Analysis for: $C_{18}H_{17}NO$: Calculated: C, 82.10; H, 6.51; N, 5.32. Found: C, 82.15; H, 6.59; N, 5.58.

The mother liquor from the crystallization of the titled product was evaporated to a solid which was subjected to an oil pump vacuum; wt.=5.0 g. The ratio of the titled product to 1,2,3,4-tetrahydro-1-(4-methoxyphenyl)cyclopent[b]indole in this material was 18:82 as determined by HPLC.

EXAMPLE 6

4,5-Dihydro-5-(4-Methoxyphenyl)-1-Benzazocine-2,6-(1H,3H)-Dione

To a stirred solution of the material (5.0 g) obtained from the mother liquor of Example 5 in dichloromethane (100 ml) at 10° under nitrogen was slowly added m-chloroperbenzoic acid (11.5 g) in dichloromethane (300 ml). The reaction was allowed to warm to room temperature and stirred for 18 hrs. The reaction solution was washed consecutively with 10% sodium sulfite solution, saturated sodium bicarbonate solution and brine. The dried ($MgSO_4$) solution was evaporated to a tacky solid; wt. 6.1 g. Slurrying with acetone gave a tan solid which was collected on a filter; wt. 2.2 g. Recrystallization from acetonitrile gave pure titled product; wt.=1.65 g (7% from 3-(4-methoxyphenyl)-1-cyclopentanone), mp=244°-245°.

Analysis for: $C_{18}H_{17}NO_3$: Calculated: C, 73.20; H, 5.80; N, 4.74. Found: C, 73.16; H, 5.69; N, 5.11.

EXAMPLE 7

4,5-Dihydro-4-(4-Methoxyphenyl)-1-Benzazocine-2,6-(1H,3H)-Dione

To 1,2,3,4-tetrahydro-2-(4-methoxyphenyl)cyclopent[b]indole (10.53 g) in dichloromethane (300 ml) cooled in ice was added m-chloroperbenzoic acid (18.68 g) in dichloromethane (500 ml) dropwise so that the reaction temperature remained between 0° and 10°. The ice bath was removed and the mixture stirred magnetically at room temperature overnight. The solution was washed consecutively with sodium sulfite solution, saturated sodium bicarbonate solution and dried ($MgSO_4$). Evaporation gave a dark foam, which was crystallized from acetone (dry ice cooling). The crude titled product was collected on a filter and washed with acetone chilled in dry ice; wt. 5.15 g (44%, crop 1), mp=136°-138°. The mother liquor was evaporated to a syrup which gave 9.27 g of a foam when subjected to an oil pump vacuum. This material in dichloromethane was applied to a column of silica gel prepacked in dichloromethane. Elution was with dichloromethane, followed by dichloromethane-ethyl acetate (9:1) to remove the product. Evaporation of appropriate fractions gave a foam which was crystallized from acetone; wt. 1.62 g (15%, crop 2), mp=137°-139°. The mother liquor gave an additional 0.3 g (2%, crop 3) of product, mp=136°-138°. The three crops of crystals were combined and recrystallized from acetone to give pure titled product; wt. 6.14 g (52%), mp=138°-140°.

Analysis for: $C_{18}H_{17}NO_3$ Calculated: C, 73.20; H, 5.80; N, 4.74. Found: C, 73.54; H, 5.78; N, 4.72.

EXAMPLE 8

1-[2-(Dimethylamino)Ethyl]-4,5-Dihydro-4-(4-Methoxy)-1-Benzazocine-2,6(1H,3H)-Dione, Maleate (1:1)

To azeotropically dried toluene (90 ml) was added 4,5-dihydro-4-(4-methoxyphenyl)-1-benzazocine-2,6-(1H,3H)-dione (3.84 g) and 60% sodium hydride in mineral oil (0.633 g) and the mixture stirred magnetically under a nitrogen atmosphere at room temperature overnight. To the mixture was addd freshly prepared N,N-dimethylaminoethyl chloride (5.1 g) dropwise and the mixture magnetically stirred and heated at 80° (under reflux) for 1 hour. A further 5.1 g of N,N-dimethylaminoethyl chloride was added and the mixture was stirred and heated at 80° for a further 1 hour. The mixture was cooled in ice and filtered through sintered glass. (The material on the filter was discarded.) The filtrate was evaporated to give a mixed oil which was subjected to an oil pump vacuum. This material was dissolved in ether and the solution filtered through Celite. The filtrate was evaporated to a biphasic oil which was subjected to an oil pump vacuum, wt. 4.88 g. To this material was added acetone (30 ml) and fumaric acid (1.55 g) and the mixture was heated to boiling. A crude fumarate salt of the titled product crystallized from the resulting solution; wt. 4.87 (78%), mp=197°-200°. Recrystallization from methanol-acetone gave a purified fumarate salt, wt.=4.27 g, mp=199°-201°.

A portion of the fumarate salt (4.23 g) was stirred with saturated sodium bicarbonate solution and ether until the solid had dissolved. The aqueous layer was separated and washed two times with ether. The ether extract and washings were washed with brine and dried ($MgSO_4$). Evaporation of the solvent gave an oil which was subjected to an oil pump vacuum; wt. 3.14 g. To this material (3.14 g) was added maleic acid (0.995 g) and acetone (6 ml) and the mixture warmed to achieve solution. Addition of ether (seeding) and acetone (as needed) caused the crystallization of a maleate salt; wt. 3.47 g (56%), mp=122°-124°. The mother liquor deposited further crystals; wt. 0.23 g., mp=122°-124°. Recrystallization of both crops of crystals from acetone-ether gave pure titled product, wt. 3.52 g (57%), mp=123°-125°.

Analysis for: $C_{22}H_{26}N_2O_3 \cdot C_4H_4O_4$: Calculated: C, 64.72; H, 6.27; N, 5.81. Found: C, 64.43; H, 6.26; N, 5.92.

EXAMPLE 9

1-[2-(Dimethylamino)Ethyl]-4,5-Dihydro-5-(4-Methoxyphenyl)-1-Benzazocine-2,6(1H,3H)-Dione To azeotropically dried 4,5-Dihydro-5-(4-methoxyphenyl)-1-benzazocine-2,6(1H,3H)-dione (1.80 g) in toluene (40 ml) was added 60% sodium hydride in mineral oil (0.27 g) and the mixture stirred under nitrogen at room temperature overnight. The slurry was stirred and heated to 70° for 15 minutes, and the freshly prepared N,N-dimethylaminoethyl chloride (1.25 g) was slowly added. After a half an hour at 70°, a further 1.25 g of N,N-dimethylaminoethyl chloride was added. The temperature was then raised to 90° and maintained for 3 hours. The cooled reaction mixture was filtered through sintered glass and the filtered solid discarded. The filtrate was evaporated and the residue was triturated with ether. The resulting white solid was collected on a filter; wt. 1.58 g (72%), mp=115-116. Recrystallization from ether gave pure titled product; wt. 1.25 g, mp=116°-117°.

Analysis for: $C_{22}H_{26}N_2O_3$: Calculated: C, 72.10; H, 7.15; N, 7.65. Found: C, 72.03; H, 7.02; N, 7.96.

What is claimed is:

1. A 4-aryl-benzazocine-2,6-dione of Formula I

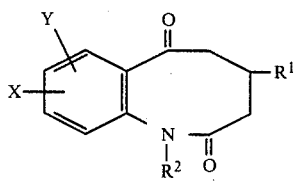

in which
- $R^1$ is phenyl, naphthyl or phenyl or naphthyl substituted by one to three moieties selected from fluoro, chloro, bromo, and alkyl or alkoxy of 1 to 4 carbon atoms;
- $R^2$ is $-R^3-NR^4R^5$, wherein $R^3$, $R^4$ and $R^5$ are, independently, straight or branched chain alkyl groups of 1 to 4 carbon atoms or $R^4$ and $R^5$ are concatenated to form a nitrogen ring having 3 to 8 carbon atoms; and
- X and Y are, independently, hydrogen, alkyl or alkoxy of 1 to 4 carbon atoms, dialkylamino or dialkylcarboxamido wherein each alkyl group has 1 to 4 carbon atoms, cyano, alkylacyl of 1 to 4 carbon atoms, fluoro, chloro, nitro, dialkylsulfonamido wherein each alkyl group has 1 to 4 carbon atoms, or alkylsulfonyl of 1 to 4 carbon atoms, os a pharmaceutically acceptable salt thereof.

2. A compound of claim 1 in which $R^1$ is phenyl or phenyl substituted by one to three moities selected from fluoro, chloro, bromo, and alkyl or alkoxy of 1 to 4 carbon atoms.

3. A compound of claim 1 in which $R^3$ is methylene or ethylene.

4. A compound of claim 1 in which $R^4$ and $R^5$ are methyl or ethyl.

5. A compound of claim 1 in which $-NR^4R^5$ is pyrrolidine, piperidine, or hexamethylimine.

6. A compound of claim 1 in which X and Y are hydrogen, lower alkyl or lower alkoxy of 1 to 3 carbon atoms, fluoro, chloro, or X is one of the foregoing and Y is hydrogen.

7. A compound of claim 1 in which $R^1$ is phenyl, naphthyl, methoxyphenyl, chlorophenyl, trimethoxyphenyl or methylnaphthyl.

8. A compound of claim 1 in which X and Y are hydrogen.

9. A compound of claim 1 which is 1-[2-(dimethylamino)ethyl]-4,5-dihydro-4-(4-methoxyphenyl)-1-benzazocine-2,6-(1H,3H)-dione.

10. A method of treating heart arrhythmia in mammals, including man, having a heart arrhythmia, comprising administering to such mammal in need thereof an amount effective to alleviate said arrhythmia of a compound of Formula I

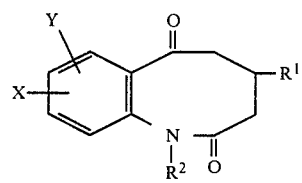

in which
- $R^1$ is phenyl, naphthyl or phenyl or naphthyl substituted by one to three moieties selected from fluoro, chloro, bromo, and alkyl or alkoxy of 1 to 4 carbon atoms;
- $R^2$ is $-R^3-NR^4R^5$, wherein $R^3$, $R^4$ and $R^5$ are, independently, straight or branched chain alkyl groups of 1 to 4 carbon atoms or $R^4$ and $R^5$ are concatenated to form a nitrogen ring having 3 to 8 carbon atoms; and
- X and Y are, independently, hydrogen, alkyl or alkoxy of 1 to 4 carbon atoms, dialkylamino or dialkylcarboxamido wherein each alkyl group has 1 to 4 carbon atoms, cyano, alkylacyl of 1 to 4 carbon atoms, fluoro, chloro, nitro, dialkylsulfonamido wherein each alkyl group has 1 to 4 carbon atoms, or alkylsulfonyl of 1 to 4 carbon atoms, or a pharmaceutically acceptable salt thereof.

11. A method according to claim 10 wherein $R^1$ of Formula I is phenyl or phenyl substituted by one to three moieties selected from fluoro, chloro, bromo, and alkyl or alkoxy of 1 to 4 carbon atoms.

12. A method according to claim 10 wherein $R^3$ of Formula I is methylene or ethylene.

13. A method according to claim 10 wherein $R^4$ and $R^5$ of Formula I are methyl or ethyl.

14. A method according to claim 10 wherein $-NR^4R^5$ of Formula I is pyrrolidine, piperidine, or hexamethylimine.

15. A method according to claim 10 wherein X and Y of Formula I are hydrogen, lower alkyl or lower alkoxy of 1 to 3 carbon atoms, fluoro, chloro, or X is one of the foregoing and Y is hydrogen.

16. A method according to claim 10 wherein $R^1$ of Formula I is phenyl, naphthyl, methoxyphenyl, chlorophenyl, trimethoxyphenyl or methylnaphthyl.

17. A method according to claim 10 wherein X and Y of Formula I are hydrogen.

18. A method according to claim 10 wherein the compound of Formula I is 1-[2-(dimethylamino)ethyl]-4,5-dihydro-4-(4-methoxyphenyl)-1-benzazocine-2,6-(1H,3H)-dione.

* * * * *